United States Patent [19]

Friemel et al.

[11] Patent Number: 5,017,376

[45] Date of Patent: May 21, 1991

[54] DELAYED HYDROLYSIS OF METAL PHOSPHIDES

[75] Inventors: Wolfgang Friemel, Heppenheim; Volker Barth, Ludwigshafen; Hildegund Dierks, Erbach, all of Fed. Rep. of Germany

[73] Assignee: Detia Freyberg GmbH, Laudenbach, Fed. Rep. of Germany

[21] Appl. No.: 420,503

[22] Filed: Oct. 11, 1989

Related U.S. Application Data

[62] Division of Ser. No. 138,772, Dec. 29, 1987, Pat. No. 4,894,230.

[30] Foreign Application Priority Data

Jan. 5, 1987 [DE] Fed. Rep. of Germany ....... 3700176

[51] Int. Cl.$^5$ .......................................... A01N 25/06
[52] U.S. Cl. .................... 424/409; 424/405; 424/408
[58] Field of Search ................. 424/40, 405, 408, 409, 424/128

[56] References Cited

U.S. PATENT DOCUMENTS

| | | | |
|---|---|---|---|
| 4,210,683 | 7/1980 | Praxel et al. | 424/128 |
| 4,347,241 | 8/1982 | Kapp | 424/128 |
| 4,664,847 | 5/1983 | Williams | 424/40 |
| 4,762,718 | 8/1988 | Marks, Sr. | 424/405 |

*Primary Examiner*—Merrell C. Cashion, Jr.
*Assistant Examiner*—Leon R. Horne
*Attorney, Agent, or Firm*—Millen, White & Zelano

[57] ABSTRACT

A method of producing an alkaline earth or alkaline earth metal phosphide-based hydrogen phosphide generating pest control agent by completely coating even surfaced bodies of the alkaline earth or alkaline earth metal phosphide with a moisture-permeable coating which delays the generation of the hydrogen phosphide therefrom for a desired period of several hours up to one month and which is formed from moisture-pervious, solid, organic materials.

30 Claims, No Drawings

DELAYED HYDROLYSIS OF METAL PHOSPHIDES

This is a division of application Ser. No. 07/138,772 filed Dec. 29, 1987 now U.S. Pat. No. 4,894,230.

BACKGROUND OF THE INVENTION

The invention relates to hydrogen phosphide generating pest control agents on the basis of alkaline earth or earth metal phosphides comprising a coating for retarding the nset of the generation of hydrogen phosphide therefrom.

Pest control agents in solid form are known which when exposed to air slowly evolve gaseous components. Such pest control agents are adapted to generate hydrogen phosphide from hydrolysable alkaline earth and/or earth metal phosphides, in particular on the basis of aluminum phosphide and magnesium phosphide, when acted upon by the moisture content of air or stored commodities. Such pest control agents are employed for example for combating pests such as e.g. bugs, worms, cockroaches or other insects and also rodents, e.g. mice and rats, e.g. in stores, mills, shipholds, railway carriages, trucks, containers, storage sheds, plastic lined earth silos and dumps or silos for grain, legumes, nuts, cocoa beans, tobacco or other foodstuffs or luxury goods, animal feeds and other processed or unprocessed commodities and various environments whether used for storage or containing such commodities or not.

Such pest control agents have in the past 10 to 20 years gained the upper hand to an increasing extent over other fumigating agents such as methyl bromide, ethylene dibromide and ethylene oxide. Reasons for this are on the one hand the favorable properties of hydrogen phosphide; i.e., it in no way impairs the quality of the fumigated commodities, and it rapidly penetrates into the interior, e.g. in the case of grain into the seeds, where it destroys animal organisms including all their development stages. However, it is dissipated just as rapidly again by aeration which follows the fumigation. On the other hand the application is relatively simple because the products, e.g. in the form of pressed bodies such as tablets and pellets can either be admixed to the flow of grain or be spread out on the floor of storage halls. However, such pest control agents can also be filled as compositions in powder form into sachets of special paper or suitable non-woven fabrics (fleeces) and can in that form be introduced into the stored commodities. The pest control agent releases the hydrogen phosphide formed by hydrolysis through the walls of the sachets to the outside. A further development of this method of application for the fumigation process involves the use of a belt comprising a multitude of pockets for the direct accommodation of the pest control agent or of sachets thereof.

Although, in contrast to the use of other gases, it is usually not necessary to wear gas-masks when employing hydrogen phosphide generating pest control agents, situations do arise when measurable hydrogen phosphide concentrations occur even during the application stage—in particular when the temperatures and moisture are relatively high.

In the light of ever-increasing environmental consciousness, this fact gives rise to increasing criticism of the use of such pest control agents, because hydrogen phosphide is highly toxic also for humans and higher animals.

The result has been that in some countries or in part of such countries labos organizations are prohibiting the application of hydrogen phosphide developing pest control agents by their members, not the least because in the past several accidents with fatal consequences occurred.

In order to mitigate the high moisture sensitivity of the abovementioned preparations during handling, packaging and application, attempts had previously been made (DE-GM 1829597) to coat the phosphide particles or the entire tablets with hard paraffin, natural or synthetic resins, waxes or silicones. For that purpose the tablets which had sharp corners and very rough surface configurations were dipped into solutions of the coating substance. The preferred embodiments provided for the incorporation of decomposable substances, e.g. ammonium carbamate for bursting open the coating. These coatings, which, if complete, were completely impervious to moisture, were unsuccessful. If the coating were thin the cover was incomplete and the tablets began to release gas immediately on exposure to moist air. Such coatings also offered no effective protection against violent reaction with liquid water. On the other hand, if the coating was relatively thick, it prevented the access of moisture to the phosphide entirely. Such tablets then did not release phosphine at all unless the coating was broken by mechanical action. From those unsuccessful attempts a further proposal arose (U.S. Pat. No. 3,132,367) to completely envelop the individual phosphide particles with a coating, in particular of hard paraffin wax. In order to permit access to the phosphide particles of ambient moisture when using the preparation, it was considered necessary to incorporate a bursting agent such as ammonium carbamate. In this regard, see U.S. Pat. No. 4,347,241, which discusses the use of a bursting agent. These coatings of moisture-impervious material, in combination with the ammonium carbamate, although intended to delay the onset of phosphine generation, did not achieve this in practice. If the mass loss of the tablets due to the loss of carbamate was taken into account it was found that these tablets in fact commenced releasing a substantial amount of phosphine within minutes of exposure to humidity and continued doing so for several days, albeit at a reduced rate and with a reduced risk of autoignition.

It was also proposed to admix the phosphide with a very slowly evaporating substance such as p-dichlorobenzene, camphor, methaldehyde and paraformaldehyde and to press the mixture into tablets (DP 1 155 631) in order to attain a retarded gas evolution. Quite apart from the fact that, because of the absence of a dense coating, the phosphide particles present on the outside of the tablets commence immediately to emit gas and therefore the aforesaid deficiencies of the prior art compositions are not eliminated, the substances proposed have all been toxic. Thus, methaldehyde for example, is employed as a poison for controlling snails. Such substances are therefore quite unsuitable for the treatment of foodstuffs such as grain, nuts or cocoa beans.

Prior to the present invention all attempts had failed to produce a metal phosphide preparation, e.g. in the form of a tablet, a tablet with a substantial "built-in" predetermined initial delay period preceding the onset of the desired phosphine generation at a normal rate—in fact, for more than 20 years the attainment of this desirable effect had been considered impossible.

GENERAL DESCRIPTION OF THE INVENTION

Surprisingly, it has now been found possible to provide metal phosphide compositions with such a "built-in" delay period and to control the length of such period substantially at will to last from several hours up to several weeks, if this is desired.

Accordingly, it is an object of the invention to provide a pest control agent based on alkaline earth or earth metal phosphides and optionally additives in which the liberation of phosphine can be delayed, e.g. until such time that no more risk exists of causing harm to personnel engaged in the application of the pest control agent, the start of the gas generation being delayed to a greater or lesser extent depending on conditions at the site of application, in some cases even by several weeks and thereby afford complete safety. Once the phosphine generation commences, it proceeds in a conventional manner and rate. This object is attained without the use of a special bursting agent.

It is another object to provide a pest control agent in which the start of the gas generation is influenced minimally by ambient temperature and the humidity.

It is another object to provide such a pest control agent which is substantially insensitive to the effect of liquid water and in particular not inclined to autoignite. It is still another object to provide such a pest control agent for which there is no need to modify the customary conditions of application of known hydrogen phosphide generating pest control agents materially.

Other objects and advantages will become apparent from what follows.

SUMMARY OF THE INVENTION

The present invention provides hydrogen phosphide generating pest control agents comprising a composition comprising hydrolyzable alkaline earth or earth metal phosphide and optionally additives and a coating thereon for retarding the gas generation, characterized by a "built-in" predetermined initial delay period of one or more hours, preferably at least three hours, during which phosphine gas generation is substantially prevented, followed by sudden bursting of the coating and commencement of generation of phosphine gas substantially uninhibited by the coating, the duration of the delay period the timing of the commencement of uninhibited generation of phosphine gas being regulated by a controlled moisture permeability of the coating, which is composed of a moisture-pervious, solid organic material which completely envelops the hydrogen phosphide generating composition.

DETAILED DISCLOSURE

During the delay period the generation of phosphine gas is substantially prevented, i.e., during the entire delay period so little phosphine is released from the composition that only minimal, normally non-hazardous phosphine concentrations will build up in the environment to which the pest control agent is exposed until bursting of the coating commences. The total amount of available phosphine of the composition is normally reduced during the delay period by less than 3%, e.g. from 1 to 2% over the entire delay period. This is even so for delay periods of up to one month.

The bursting of the coating when it occurs, takes place relatively rapidly and suddenly, starting with the appearance of usually visible holes in the coating and the development of progressively larger cracks and apertures.

Even compositions based on magnesium phosphide can now be made with delay periods exceeding one hour, 3 hours, and, if so desired, even more.

The preferred embodiments, particularly those based on aluminum phosphide, have a predetermined initial delay period of more than 5 hours, e.g. at least 6 hours, preferably from 8 hours up to several days, e.g. 2 to 3 days, and in special cases even up to 3-4 weeks, i.e. up to 1 month.

The invention, according to a further aspect thereof, also provides a method of providing a hydrogen phosphide developing pest control agent comprising a composition based on hydrolyzable alkaline earth or earth metal phosphides and optionally additives with a "built-in" predetermined initial delay period of one or more hours during which phosphine gas generation is substantially prevented, which comprises completely enveloping the agent in the form of bodies having even and rounded outlines in a coating having a controlled moisture permeability, being composed of a moisture-pervious, solid organic material, forming a continuous film.

According to a preferred embodiment, the pest control agents are provided in the form of pressed bodies of even outlines having rounded edges or as a powder having a coating applied thereon, resulting in a coated granulate. Aluminum phosphide, respectively magnesium phosphide is/are preferably used as the earth metal phosphide, respectively alkaline earth phosphide.

The preferred feature of even outlines, i.e. a smooth surface configuration, preferably combined with an absence of sharp corners, due to the rounded edges greatly facilitates the reliable attainment of the required coating quality which while having a predetermined, restricted permeability to water vapor completely envelopes the metal phosphide and thus prevents the onset of uninhibited phosphine generation. The prior art coated tablets had sharp edges and a very rough surface.

Since the desired retardation can be attained even without a bursting agent by coating the substance which generates hydrogen phosphide, respectively the composition which generates hydrogen phosphide, with the recommended moisture-pervious, solid, organic materials, the pest control agent according to the invention need not contain any bursting agent. Indeed, the presence of any bursting agent such as ammonium carbamate in the coating itself (as was normally the case in prior art tablets and pellets) should be avoided, because these substances result in uncontrolled perforations of the coatings.

According to the invention, it is possible to use as the organic material, e.g. an acrylic resin, in particular a polymer on the basis of acrylic acid, respectively acrylic acid derivative(s). An acrylic acid ester/methacrylic acid ester copolymer is preferred, in particular one having 1 to 4 carbon atoms in the ester group, the ester group being optionally substituted with one or more amino groups present in the form of a salt. An organic material is particularly preferred which comprises the following repetitive moieties

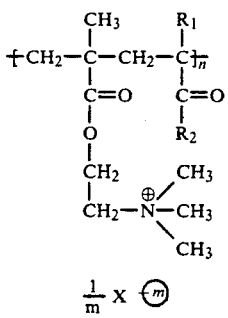

wherein $R_1$ represents hydrogen or methyl, $R_2$ represents methoxy or ethoxy and $X^{-m}$ represents an anion, wherein m denotes a numerical value of 1-3 and n represents a numerical value such that the copolymer has an average molecular mass of 50 000 to 500 000.

Also suitable are resins of the above general formula in which $R_2$ represents propyl, or isopropyl, butyl or an isomer of butyl. $R_2$ may also be a lower alkoxy group, e.g. methoxy or one of its higher homologues, e.g. up to $C_4$. The amino ethoxy group in the above general formula may optionally be replaced, by higher or lower homologues, e.g. having up to 4 carbon atoms, or by hydroxy.

These resins may more generally be defined as an acrylic resin having the following repetitive copolymer moieties

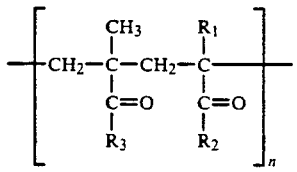

wherein $R_1$ represents an alkyl group having 1 to 4 carbon atoms or hydrogen, $R_2$ represents an alkoxy group having 1 to 4 carbon atoms and $R_3$ represents hydroxyl or an aminoalkoxy group, optionally methyl substituted and optionally quarternary ammonium kation, in the form of an addition salt with an anion and n represents a numerical value such that the copolymer has an average molecular mass of 50,000 to 500,000.

The different possibilities may be present in the lacquer forming resin as copolymers or as mixtures of such different polymers or copolymers. Resins as set out above are available commercially.

The ammonium groups and their amounts may be selected to influence the moisture permeability of the coating. They may for example have a ratio of OH to alkoxy of 1:1 to 1:2.

Also suitable as the organic material is e.g. a styrene resin, in particular styrene maleic acid anhydride copolymer, a cellulose derivative, a cellulose ester, in particular cellulose acetate or polyvinyl acetate or polyvinyl acetate phthalate or a combination of two or more of these. Also suitable as the organic material is colophonium, preferably in combination with an anti-adhesive agent, and/or an alkylcellulose ester, optionally substituted, the latter being preferably hydroxypropyl methylcellulose phthalate (HPMCP), optionally mixed with ethyl cellulose. Particularly preferred are those solid organic materials, wherein the cellulose derivative or cellulose ester or alkyl cellulose ester is hydroxy propylmethyl cellulose or its phthalate, or cellulose acetate phthalate or cellulose methylphthalate, mixtures of two or more of these, and all of the aforegoing optionally in a mixture with ethyl cellulose.

In contrast to the above described prior art, paraffin alone and similar low molecular weight waxes alone are not suitable as coating substances used in accordance with the invention because they do not lend themselves to the formation of films of satisfactory quality and readily controlled moisture permeability. However, these substances can be used in mixture to modify the properties of the lacquer-forming high molecular weight organic solids which are suitable.

For producing the pest control agent according to the invention, the organic material is dissolved or suspended advantageously in suitable solvents, such as alcohols, ketones or chlorinated hydrocarbons or mixtures of such solvents. The concentration of organic material in the solution in this context amounts to between 1 and 50%, in particular between 2 and 12%, preferably between 3 and 6%.

The preferred organic solid material is a synthetic lacquer-forming resin, soluble in organic solvents, optionally in admixture with stearic acid, cetyl alcohol or solid homologues thereof.

The solution of the organic material is sprayed advantageously onto the hydrogen phosphide generating substance, respectively the hydrogen phosphide generating composition provided in the form of pressed bodies or powders or granulates. The coating of powders according to the invention causes the powder particles to aggregate and results in the formation of coated granulates. Generally, pressed bodies such as pellets and tablets are preferred because they are more easily provided with the quality of coating required for a well-defined delay period.

This process can be carried out with commercially available coaters. These may comprise a bowl or drum of various shapes and configurations. Coaters are preferred in which the material to be coated is sprayed with the coating material and dried, while maintained in an agitated state of movement, preferably in a bed and more particularly a fluidized bed. In the preferred procedure air is blown into an approximately spherical container to attain a fluidization of the material to be coated. Simultaneously, the dilute solution of the organic coating material is introduced through a spray nozzle into the fluidized bed in which the pressed bodies or powder are coated. In the course thereof the solvent is immediately evaporated by the preheated airflow and a fine coating is formed. In this context it is advantageous for a plurality of coating layers to be formed successively, which can be done in a single process step or intermittently in a plurality of process steps.

In the latter case the purpose of the first coating application is to achieve a rapid covering of the core of the body of composition, to protect that core, e.g. against abrasion in the further coating procedure.

The first coating is applied, preferably using a first solution having a concentration of 8 to 50% solid organic material, more usually 8 to 30%, in particular from 10 to 24%, preferably 12 to 18%.

The second coating layer is applied, preferably, using a second solution having a concentration of from 2 to 12%, particularly from 3 to 8%, preferably 4 to 6%.

Eventually the complete coating is advantageously present in an amount of 1 to 20% by mass, preferably of 2.5 to 15% by mass based on the overall mass of the hydrogen phosphide generating composition. Preferably the coating has a film thickness of 0.1 to 2.0 mm, more usually 0.02 to 1.5 mm and preferably 0.04 to 0.5 mm. The coating material when sprayed as a film of the same thickness onto a smooth support has a water vapour permeability of 20 to 1000 g/m$^2$, more usually 50 to 600 g water per m$^2$ per 24 hours, and in particular 100 to 500 g water per m$^2$ per 24 hours.

The rate at which the atmospheric or ambient humidity diffuses through this coating, depends substantially on its thickness. Generally speaking, the beginning of the gas generation can be delayed by a period which gets longer as the thickness of the coating is increased. A further possibility to vary the period of time at which gas generation commences, is afforded by varying the composition of the coating, in particular by the addition of hydrophobizing additives. The moisture permeability of the coating also depends on the coating procedure employed. The time until gas generation commences, can be regulated in a simple and reliable manner with the pest control agents according to the invention, depending on requirements.

This can be achieved purely by trial and error, using relatively simple routine experiments.

A measure of prediction is also possible on the basis of the following principles:

1. All other parameters being equal (coating composition, coating procedure), the delay period (i.e. the period of exposure to humidity before intensive phosphine generation commences) is a non-linear function of the coating thickness. The permeability in turn is approximately inversely proportional to the coating thickness.
2. There are indications that in many cases (at least by rough approximation) where coating compositions and methods are the same, the logarithm of the delay period is inversely proportional to the square root of the film permeability and directly linearly proportional to the square root of the film thickness.
3. Qualitative comparisons of film permeabilities for water vapor (per m$^2$ per day) are possible on the basis of permeabilities in accordance with an adaptation of DIN 53122. These tests are carried out on films made by spray-coating the coating material onto a vapor pervious smooth support, having a permeability substantially higher than that of the film. The permeabilities of the coatings on the pellets or tablets are somewhat different, however, from those of the test films because these coatings are formed under different conditions.
4. Final adjustments as to film composition and thickness are then made by trial and error.

The delay period also depends on the dimensions of the bodies. For a coating of a given moisture permeability and a given shape of the body there is direct non-linear relationship between the size of the body and the delay period. This is probably due to the fact that the volume increases in proportion to the cube of the linear dimensions, while the surface area of the coating changes in proportion to the square thereof. Moreover, in larger pressed bodies a higher proportion of the hydrolyzable metal phosphide is further removed from the surface than in smaller bodies and is therefore less readily accessible to moisture which diffuses through the coating. In addition it is easier to apply thick coatings onto large bodies (particularly those having rounded outlines) than onto small bodies, and substantially less coating material based on metal phosphide is needed. Therefore, if it is desired to achieve very long delay periods it is advisable to increase the sizes of the bodies, e.g. to employ 3 g tablets instead of 0.6 g pellets.

If a particularly long delay of the gas generation is desired, the invention also provides that an organic material is used comprising a polymer, in particular acrylic resin, in combination with stearin (stearic acid) or cetyl alcohol. Technical grades of stearic acid or cetyl alcohol are usually mixtures of solid homologues, and obviously such solid homologues and their mixtures are suitable as well. Preferably the ratio of acrylic resin to stearin or cetyl alcohol is in the range 0.5:1 to 2:1. The addition of stearin or cetyl alcohol brings about the delay of the gas generation to such a high extent that it is justified to speak of a synergistic effect.

If for example, a coating of 6% copolymer plus 6% magnesium stearate is used, based on the mass of the pressed body or powder as the coating, one may expect a delay period of about 18 hours until the coating breaks up in the case of standard pellets. A coating of 6% stearic acid alone (disregarding other shortcomings) resulted in a delay of about 10 to 20 hours.

However, if both were used in combination, i.e. 6% copolymerization product, 6% magnesium stearate and 6% stearin, there resulted a delay period of up to 23 days. Similar observations were made with the addition of cetyl alcohol.

An addition of aluminum stearate or magnesium stearate or equivalent water in soluble metal soap to the coating composition prevents the sticking together of the moulded bodies or the powder during spraying of the solution and subsequent drying. Talcum can be used for the same purpose with similar effect. In order to increase the resiliency of the coating, it is possible also to add small amounts of plasticizer, such as e.g. dibutylphthalate or dimethylphthalate. An addition of polyethylene wax has an additional sealing effect and increases the luster. Furthermore, the additional use of suitable coloring matter can be advantageous. This may serve for example as a color code for the easy identification of compositions according to the invention having different delay periods.

Also, the hydrogen phosphide generating composition may contain in addition conventional or advantageous additives. These include preferably an additive or a combination of additives selected from urea, sodium chloride, microcrystalline cellulose, lactose or preferably a stearate serving as pressing agent, ammonium biphosphate, sodium bicarbonate, sodium carbonate or ammonium carbaminate as autoignition preventing additive, paraffin wax as a hardener and/or polyethyleneglycol, preferably having a molecular mass in excess of 5,000.

Only, once, due to the reaction of the phosphide with the water vapor a certain amount of aluminum, respectively magnesium hydroxide has been formed, the coating automatically bursts open. Thereafter, once the coating has been burst open in several places in a short period, water vapor gains free access to the phosphide and the gas generation from then on proceeds approximately like that of a pressed body or powder or granulate according to the state of the art.

Because the timing of the rupturing depends only on the diffusion of the water vapor through the coating, the environmental temperature and humidity have relatively little influence in practice. The amount of liberated hydrogen phosphide until the coating burst open, is so small that the desired safety in use and handling is afforded. In a preferred embodiment the bursting open and gas generation procedure commence only after 8 hours, i.e. after a full working day. This ensures that the workers who carry out the spreading out of the hydrogen phosphide generating composition are not exposed to any gas concentration giving rise to concern.

In a further embodiment the bursting open procedure is delayed by 24 hours. During that period silo compartments and shipholds can be filled. Pressed bodies having a delayed gas generation may then be admixed to the inflowing stream of grain and practically no gas is released during the loading process.

In the case of large objects such as steel tanks or storage dumps the charging may last up to 7 days. A premature gas generation by pressed bodies added to the grain stream would not only result in hazards to the environment, but would also negate completely the success of the fumigation, because normally such conventional pressed bodies or powders have released all their gas after 2 to 3 days. For that reason it was previously not possible to fumigate such objects during charging.

However, by means of pressed bodies, respectively powders or granulates coated in accordance with the invention, it is possible to delay the gas generation due to the delayed rupturing of the coating by up to several weeks, so that henceforth such fumigations are also readily feasible.

According to the invention, it is thus possible to attain at will delay periods ranging from several hours to several weeks, and the pest control agents according to the invention, can be adapted to the prevailing requirements which are dictated by various storage conditions and details of practice.

A further material technical advance of the preferred pest control agents according to the invention resides in that their coatings are quite insensitive to liquid water. Accordingly, they are also suitable for use in the open air for the control of rodent pests such as rats and voles. Placing the product is even possible in rain or in very damp soil, without this resulting as in the past in premature release of amounts of hydrogen phosphide which would be dangerous to the applicator. The undesirable occurrence of auto-ignition which in the past was regularly experienced with pest control agents of the type referred to in the introduction whenever liquid water enters into reaction with easily hydrolyzable phosphides, can be avoided to a fargoing degree with the products according to the invention. Independently of the object to provide pest control agents with a delayed gas release, the aforegoing is a further object of the pest control agent according to the invention.

Relatively long delay periods are desirable for specialized uses such as the control of socalled "mountain beavers" a serious rodent pest in North America. For that purpose the pest control agent is, for example, hidden in nest-making material which the mountain beavers take down into their burrows. The delay period prevents the animals from being forewarned of the dangers by the smell of phosphine, because the invention prevents the premature release of phosphine in large concentrations.

DESCRIPTION OF SPECIFIC EXAMPLES

The following examples 1 to 7 illustrate coating compositions according to the invention. In the present examples, unless otherwise stated, all percentages of the coating compositions are percentages by weight based on the weight of the pressed bodies pest control agents according to the invention. The compositions are unless otherwise stated, in the form of pellets of 0.6 g each, 8.7 mm diameter, 7 mm high, radius of curvature of the end faces 7.2 mm, height of cylindrical central portion 4.4 mm.

The incorporation of plasticisers in Examples 1 to 7 improves the durability of the coating for transport purposes but is not essential.

AMC as used in these examples was in accordance with the general formula further above.

| | Mass % | Coating thickness | Delay period up to bursting open of coating |
|---|---|---|---|
| Example 1 | | | |
| Acrylic acid ester/ metacrylate copolymer (AMC) | 1.20 | 5.8 gm/cm$^2$ | 6-8 hours |
| Magnesium stearate | 1.20 | | |
| Plasticiser | 0.12 | 0.047 mm | |
| Example 2 | | | |
| AMC | 0.70 | 5.2 mg/cm$^2$ | 8 hours |
| Magnesium stearate | 1.00 | | |
| Stearin | 0.50 | 0.042 mm | |
| Plasticiser | 0.07 | | |
| Example 3 | | | |
| AMC | 2.00 | 9.1 mg/cm$^2$ | 24 hours |
| Magnesium stearate | 1.25 | | |
| Stearin | 0.50 | 0.073 mm | |
| Plasticiser | 0.20 | | |
| Example 4 | | | |
| AMC | 3.50 | 12.4 mg/cm$^2$ | 48 hours |
| Magnesium stearate | 1.50 | | |
| Plasticiser | 0.35 | 0.099 mm | |
| Example 5 | | | |
| AMC | 4.50 | 32.2 mg/cm$^2$ | 7 days |
| Magnesium stearate | 4.50 | | |
| Stearin | 4.50 | 0.258 mm | |
| Plasticiser | 0.45 | | |
| Example 6 | | | |
| AMC | 6.00 | 41.7 mg/cm$^2$ | 23 days |
| Magnesium stearate | 6.00 | | |
| Stearin | 6.00 | 0.333 mm | |
| Plasticiser | 0.6 | | |
| Example 7 | | | |
| AMC | 6.00 | | 20-23 days |
| Magnesium-Stearate | 6.00 | 42.9 mg/cm$^2$ | |
| Cetyl alcohol | 6.00 | | |
| Plasticiser | 0.60 | 0.343 mm | |

The examples which now follow also illustrate the process of manufacture of the coatings. In those examples where coating permeabilities are given, these were determined by spraying a coating of the same thickness and composition onto a smoothly calendered nonwoven plastics web (HDPE fleece, 112 g/m$^2$) of high water vapor permeability and subjecting the so coated web to measurement, using the apparatus and method in accordance with DIN 53122 (Nov. 1974). It is measured in terms of g H$_2$O/m$^2$ (over a period of 24 hours).

EXAMPLE 8

Pellets sample K28

Aluminum phosphide pellets of standard size and composition were coated in a fluidized bed apparatus using dual spray nozzles. The following coating solutions were used:
Solution 1:
1.0% AMC, 1% magnesium stearate; 0.1% dibutyl phthalate; 0.02% zapon blue, 12.5% methylene chloride
Solution 2:

2.0% stearin; 3.5% AMC; 3.5% magnesium stearate; 0.35% dibutyl phthalate; 0.02% zapon blue; dissolved in 80% methylene chloride.

The air passing through the fluidized bed was kept at approximately 45° to 55° and after 15 minutes reached equilibrium at 54° to 55° C. resulting in a product temperature of about 44° to 46° C. Solution 1 was introduced during the first 5 minutes and solution 2 had been fully introduced after 34 minutes. This was followed by 3 minutes drying at the same temperature, whereafter the air temperature was reduced to 25° C. until the product had been cooled. The tablets carried a coating of about 26.42 mg/cm$^2$ corresponding to a coating thickness of about 0.21 mm. The water vapor permeability of the coating was 115.6 g H$_2$O/m$^2$. The delay period was approximately 7 days.

EXAMPLE 9

Sample H3

Spherical Tablets

The tablets were of standard aluminum phosphide formulation and standard mass of 3.0 g having a diameter of 15.7 mm and a thickness of 15.4 mm. The end faces were spherical, separated by cylindrical side walls approximately 3 mm high.

Coating took place in a horizontally mounted rotary coating drum having perforated drum walls for the introduction and discharge of air. The air temperature was initially 30° C. and progressively raised to about 42° C. The following coating solution was sprayed into the apparatus containing 10 kg tablets over a period of 175 minutes:

900 g stearin (9.0%), 600 g magnesium stearate (6.0%), 300 g AMC (3.0%), 30 g dibutyl phthalate (0.3%); all dissolved in 8000 g methylene chloride.

This resulted in a coating thickness of about 88.3 mg/cm$^2$, i.e. a coating thickness of about 0.7 mm. These tablets yielded a delay period of about 100 hours.

EXAMPLE 10

Pellets

Sample A20/1

Standard aluminium phosphide pellets containing 70% technical aluminum phosphide were coated in a tablet coating pan using the following solutions (based on 3 kg pellets):

Solution 1:

30 g AMC (1.0%), 30 g magnesium stearate (1.0%), 3 g dibutyl phthalate (0.1%), dissolved in 375 g methylene chloride.

Solution 2:

75 g AMC (2.5%), 75 g magnesium stearate (2.5%), 7.5 g dibutyl phthalate (0.25%) dissolved in 2400 g methylene chloride.

The first solution was sprayed into the drum during the first 7 minutes, followed by 5 minutes drying at minimum rate of rotation. The second solution was introduced over a period of 69 minutes followed by 3 minutes drying with warm air and 7 minutes cooling. The coating thickness was 17 mg/cm$^2$, corresponding to a coating thickness of about 0.136 mm. The delay period was between 55 and 70 hours.

EXAMPLE 11

Pellets

Sample A5/39

1 kg standard pellets were coated in a tablet coating pan using the following solution:

10 g AMC (1.0%), 15 g stearin (1.5%), 15 g magnesium stearate (1.5%), 1 g dibutyl phthalate (0.1%), 0.1 g zapon blue (0.01%) dissolved in 800 g methylene chloride. Spraying proceeded for 27 minutes followed by 5 minutes drying whereafter a further 15 g (1.5%) of magnesium stearate dissolved in 200 g methylene chloride were sprayed on in the course of a further 7 minutes. The total coating thickness was 9.46 mg/cm$^2$, i.e. approximately 0.076 mm. The delay period was about 10 to 12 hours.

EXAMPLE 12

Pellets

Sample A5/48

1000 g standard aluminum phosphide pellets were coated in a tablet coating pan using the following solution:

Solution 1:

15 g AMC (1.5%), 15 g magnesium stearate (1.5%), 1.5 g dibutyl phthalate (0.15%), 0.1 g zapon blue (0.01%) dissolved in 600 g methylene chloride.

Solution 2:

10 g HPMCP (1.0%) dissolved in 250 g methanol/methylene chloride (30:70).

The first solution was applied over a period of 31 minutes followed by 5 minutes drying. The second solution was introduced over a period of 9 minutes followed by 1 minute drying with hot air and 9 minutes with cold air. The total coating thickness was 9.6 mg/cm$^2$ equivalent to about 0.079 mm. The delay period was about 5 hours.

EXAMPLE 13

Aluminum Phosphide Pellets

Sample A5/30

500 g standard aluminum phosphide pellets were coated in a tablet coating drum using the following solution:

7.5 g AMC (1.5%), 33.75 g magnesium stearate dispersion (equivalent to 1.5% magnesium stearate), 0.75 g dibutyl phthalate (0.15%) and coloring matter, dissolved in 400 g methylene chloride. The solution was introduced by slowest possible spraying over a period of 32 minutes followed by 20 minutes drying. The coating thickness was about 7.3 mg/cm$^2$, i.e. about 0.06 mm. The delay period was between 4 an 5 hours.

EXAMPLE 14

Aluminum Phosphide Pellets

Sample A5/30I

Example 13 was repeated except that magnesium stearate was replaced by 1.5% micro talcum. A batch of 1 kg pellets was coated with the above substances dissolved and dispersed in 800 g methylene chloride sprayed into the drum over a period of 25 minutes, followed by 3 minutes drying with hot air and a further 2 minutes cooling. The coating had a thickness of 73 mg/cm² equivalent to about 0.06 mm. The delay period was between 5 and 6 hours.

EXAMPLE 15

Aluminum Phosphide Pellets

Sample A10/10

The pellets were coated with a solution of 6.0% AMC, 6.0% magnesium stearate, 6.0% stearin, 0.1% colouring matter and 81.9% methylene chloride, all based on weight of pellets sprayed into the drum over a period of 30 minutes followed by 1 minute drying with hot air and 30 minutes without any air. The coating thickness was 41.5 mg/cm² equivalent to about 0.33 mm and the delay period was approximately 20 days.

EXAMPLE 16

Aluminum Phosphide Pellets

Sample A10/3

The pellets were coated in a tablet coating drum with 6.0% AMC, 6.0% magnesium stearate, 6.0% stearic acid, 0.6% dibutyl phthalate and 81.4% methylene chloride introduced as follows in stages: 7 minutes spraying followed by 3 minutes drying, 5 minutes spraying followed by 2 minutes drying with hot air, 5 minutes spraying followed by 30 minutes drying an a further 10 minutes drying with hot air while keeping the drum turning at 60 rpm. The coating thickness was 43 mg/cm² corresponding to about 0.34 mm. The delay period was about 23 days.

EXAMPLE 17

Aluminum Phosphide Pellets

Sample A5/31

500 g pellets were coated in a tablet coating drum using a solution of 1.2% AMC, 1.2% magnesium stearate (dispersion), 0.12% dibutyl phthalate and colouring matter (the aforegoing based on weight of pellets) dissolved in 400 g methylene chloride. The solution was sprayed into the drum over a period of 28 minutes, followed by 20 minutes drying at minimum rate of rotation.

The coating thickness was 5.8 mg/cm² equivalent to about 0.046 mm. The water vapor permeability of the coating was 464.2 g $H_2O/m^3$. The delay period was between 6 and 8 hours.

EXAMPLE 18

Aluminum Phosphide Pellets

Sample H8

6000 g pellets were sprayed in a fluidized bed coating apparatus with the following solution: 60.0 g AMC, 90.0 g stearin, 90.0 g magnesium stearate, 6.0 g dibutyl phthalate, 0.6 g zapon blue, 4.800 g methylene chloride. Spraying was completed after 34 minutes, followed by 4 minutes of drying. The coating thickness was 9.5 mg/cm² equivalent to about 0.076 mm. The delay period was between 6 and 8 hours.

EXAMPLE 19

Magnesium Phosphide Pellets

Sample $Mg_3P_2$-P 500 g pellets (containing 34% magnesium phosphide) were coated in a coating drum with the following solution: 17.5 g AMC (3.5%), 17.5 g magnesium stearate (3.5%), 1.75 g dibutyl phthalate (0.35%), 0.05% zapon blue, dissolved in 400 g methylene chloride. The solution was sprayed into the drum over a period of 8 minutes followed by 3 minutes drying. The coating thickness was 17 mg/cm² equivalent to about 0.14 mm. The delay period was 2 hours (during which period uncoated pellets would already have released approximately ⅓ of their available phosphine content).

EXAMPLE 20

Aluminum phosphide pellets

Sample A5/44

1 kg standard aluminum phosphide pellets were coated in a tablet coating drum using the following solutions: 12.5 g HPMCP (Hydroxypropylmethylcellulosephthalate) (1.25%) dissolved in 125 g methanol/methylene chloride (30:70).

Second solution:

22.5 g HPMCP (2.25%), 0.1 g zapon blue (0.1%), dissolved in 800 g methanol/methylene chloride (30:70).

Solution 1 was sprayed into the drum in 4 minutes, followed by solution 2 in 41 minutes, followed in turn by 2 minutes drying with hot air and 5 minutes cooling.

The coating thickness was about 8.1 mg/cm² equivalent to about 0.072 mm. The delay period was between 15 and 24 hours.

The above examples are to be read in conjunction with the general description of the invention. Coating substances other than those described in the specific examples can be applied in substantially analogous manners, due provision being made for the properties of the coating substances. For example, coating substances which are very sticky necessitate the use of anti-adhesive additives.

It will be apparent from the aforegoing that the present invention provides a convenient new method for regulating at will the time of commencement of normal phosphine release from pest control agents comprising compositions based on hydrolyzable metal phosphides, in particular alkaline earth or earth metal phosphides and optional additives following a predetermined delay period during which the release of phosphine is negligible, by completely enveloping these compositions, preferably in the form of pressed bodies, i.e. smooth surface outlines having rounded edges, with a coating of controlled water vapor permeability comprising a water vapor pervious solid organic material and preferably containing no bursting agent of any kind, the composition being used by being exposed to moisture, substantially in the conventional manner.

What we claim is:

1. A method of producing an alkaline earth or alkaline earth metal phosphide-based hydrogen phosphide generating pest control agent, which comprises coating each of a plurality of molded or shaped even surfaced bodies of a hydrolyzable alkaline earth or earth metal phosphide with an uninterrupted coating of a moisture permeable solid organic material which initially restricts and later permits free access of moisture to the phosphide, thereby retarding the phosphine gas generation for an initial delay period after the pest control agent is exposed to ambient moisture of one or more hours, during which delay period phosphine gas generation is substantially prevented and after which delay period bursting of the coating occurs and generation of phosphine gas begins substantially uninhibited by the coating, the duration of the delay period and the timing of the commencement of uninhibited generation of phosphine gas being determined by the moisture permeability of the coating.

2. A method according to claim 1, wherein the bodies are pressed bodies of smooth and rounded surface configuration and the coating material has a moisture permeability of 20 to 1000 g $H_2O/m^2/24$ hours, as a continuous film sprayed onto a smooth support.

3. A method according to claim 1, wherein the coating is applied to the bodies by spraying a solution of the solid organic material in an organic solvent onto the bodies while the bodies are maintained in an agitated state of movement and the solvent is evaporated.

4. A method according to claim 3 wherein the agitated state is a fluidized bed.

5. A method according to claim 3 wherein the coating is applied as a succession of layers of the organic material.

6. A method according to claim 1, wherein the organic solid material is a synthetic lacquer-forming resin, soluble in organic solvents or a mixture thereof with stearic acid, cetyl alcohol or a solid homologue thereof.

7. A method according to claim 1, wherein the organic material is an acrylic resin.

8. A method according to claim 1, wherein the solid bodies have even and rounded outlines.

9. A method according to claim 1, wherein the coating is water-insoluble and impervious to liquid water.

10. A method according to claim 1, wherein the coating imparts an initial delay period of more than 5 hours and up to 1 month.

11. A method according to claim 1, wherein the pest control agent contains no bursting agent.

12. A method according to claim 1, wherein the organic material is an acrylic resin or an acrylic acid ester/methacrylic acid ester copolymer having 1 to 4 carbon atoms in the ester group.

13. A method according to claim 1, wherein the organic material is an acrylic acid ester/methacrylic acid ester copolymer having 1 to 4 carbon atoms in the ester group and is substituted in an ester group with one or more amino groups in the form of a salt.

14. A method according to claim 13, wherein the organic material comprises the following repetitive moieties:

$$\left[ \begin{array}{cc} CH_3 & R_1 \\ | & | \\ -CH_2-C-CH_2-C- \\ | & | \\ C=O & C=O \\ | & | \\ O & R_2 \\ | \\ CH_2 \quad CH_3 \\ | \quad \oplus \diagup \\ CH_2-N-CH_3 \\ \diagdown \\ CH_3 \end{array} \right]_n \frac{1}{m} X^{\ominus m}$$

wherein $R_1$ represents hydrogen or methyl, $R_2$ represents methoxy or ethoxy and $X^{-m}$ represents an anion, wherein m denotes a numerical value of 1-3 and n represents a numerical value such that the copolymer has an average molecular mass of 50,000 to 500,000.

15. A method according to claim 12, wherein the organic material comprises an acrylic resin having the following recurring unit $$\left[ \begin{array}{cc} CH_2 & R_1 \\ | & | \\ -CH_2-C-CH_2-C- \\ | & | \\ C=O & C=O \\ | & | \\ R_3 & R_2 \end{array} \right]_n$$

wherein $R_1$ represents an alkyl group having 1 to 4 carbon atoms or hydrogen, $R_2$ represents an alkoxy group having 1 to 4 carbon atoms and $R_3$ represents hydroxyl or an aminoalkoxy group, in the form of an addition salt with an anion and n represents a numerical value such that the copolymer has an average molecular mass of 50,000 to 500,000.

16. A method according to claim 1, wherein the organic material is one or more of a styrene resin, a cellulose derivative a cellulose ester, polyvinyl acetate or polyvinyl acetate phthalate.

17. A method according to claim 16, wherein the styrene resin includes a styrene maleic acid anhydride copolymer.

18. A method according to claim 1, wherein the organic material comprises colophonium, alone or in combination with an anti-adhesive agent, and/or an alkylcellulose ester.

19. A method according to claim 1, wherein the organic material comprises a cellulose derivative selected from the group consisting of one or more of hydroxy propyl methyl cellulose, hydroxy propyl methyl cellulose phthalate, cellulose acetate phthalate, and a mixture thereof with ethyl cellulose.

20. A method according to claim 1, wherein the organic material comprises a polymer in combination with stearin or cetyl alcohol or solid homologue thereof.

21. A method according to claim 20, wherein the polymer is an acrylic resin and the ratio of acrylic resin to stearin or cetyl alcohol or homologue thereof is in the range 0.5:1 to 2:1.

22. A method according to claim 1, wherein the coating comprises at least one of aluminum stearate, magnesium stearate or a polyethylene wax and a plasticizer.

23. A method according to claim 22, wherein the coating comprises as a plasticizer dibutyl phthalate or dimethylphthalate or equivalent dialkyl phthalate.

24. A method according to claim 1, wherein the coating is present in an amount of 1 to 20 mass percent, based on the overall mass of the composition.

25. A method according to claim 1, wherein the coating is present in an amount of from 2.5 to 15 mass percent based on the overall mass of the composition.

26. A method according to claim 1, wherein the coating has a film thickness of 0.01 to 3 mm, which coating when sprayed as a film of the same thickness on a smooth support has a water vapor permeability of 1000 to 20 g water/$m^2$/24 hours.

27. A method according to claim 1, wherein the alkaline earth or earth metal phosphide is aluminum phosphide or magnesium phosphide or a mixture thereof.

28. A method according to claim 27, wherein the composition contains a combination of additives selected from urea, sodium chloride, microcrystalline cellulose, lactose or a stearate as a pressing agent, ammonium biphosphate, sodium bicarbonate, either sodium carbonate or ammonium carbaminate as ignition retarding agent, paraffin as a hardener and polyethyleneglycol having a molecular mass in excess of 3,000.

29. A method according to claim 1, wherein the solid bodies are in the form of a coated granulate.

30. A method according to claim 1, wherein the solid bodes are in the form of pressed bodies of even outlines having rounded edges.

* * * * *